(12) United States Patent
Takamura et al.

(10) Patent No.: US 9,206,117 B2
(45) Date of Patent: Dec. 8, 2015

(54) URETHANE ACRYLATE, AND REACTIVE COMPOSITION CONTAINING SAME

(71) Applicant: DAI-ICHI KOGYO SEIYAKU CO., LTD., Kyoto-shi, Kyoto (JP)

(72) Inventors: Naohiro Takamura, Kyoto (JP); Masato Kameda, Kyoto (JP)

(73) Assignee: DAI-ICHI KOGYO SEIYAKU CO., LTD., Kyoto (JP)

( * ) Notice: Subject to any disclaimer, the term of this patent is extended or adjusted under 35 U.S.C. 154(b) by 0 days.

(21) Appl. No.: 14/428,762

(22) PCT Filed: Oct. 10, 2013

(86) PCT No.: PCT/JP2013/077560
§ 371 (c)(1),
(2) Date: Mar. 17, 2015

(87) PCT Pub. No.: WO2014/061539
PCT Pub. Date: Apr. 24, 2014

(65) Prior Publication Data
US 2015/0225338 A1  Aug. 13, 2015

(30) Foreign Application Priority Data
Oct. 17, 2012  (JP) ................ 2012-229789

(51) Int. Cl.
*C08G 18/67* (2006.01)
*C08F 290/06* (2006.01)
*C07C 271/24* (2006.01)
*C08G 18/75* (2006.01)
*C08G 18/79* (2006.01)
*C08G 18/81* (2006.01)
*C09D 175/16* (2006.01)

(52) U.S. Cl.
CPC ............. *C07C 271/24* (2013.01); *C08F 290/06* (2013.01); *C08G 18/675* (2013.01); *C08G 18/755* (2013.01); *C08G 18/792* (2013.01); *C08G 18/815* (2013.01); *C09D 175/16* (2013.01)

(58) Field of Classification Search
None
See application file for complete search history.

(56) References Cited

U.S. PATENT DOCUMENTS

2008/0131674 A1 * 6/2008 Kondo et al. ................ 428/212
2010/0189960 A1    7/2010 Yoshida et al.

FOREIGN PATENT DOCUMENTS

| JP | 2004-338214 | 12/2004 |
| JP | 2005-015621 | 1/2005 |
| JP | 2009-040955 | 2/2009 |
| JP | 2012-180487 | 9/2012 |
| WO | 2008/156115 | 12/2008 |

OTHER PUBLICATIONS

International Search Report for PCT/JP2013/077560, dated Nov. 5, 2013, and English translation.

* cited by examiner

*Primary Examiner* — Yevegeny Valenrod
(74) *Attorney, Agent, or Firm* — Wenderoth, Lind & Ponack, L.L.P.

(57) ABSTRACT

The present invention is directed to a urethane acrylate containing a reaction product of an alkylene oxide-modified dipentaerythritol (meth)acrylate.

4 Claims, No Drawings

URETHANE ACRYLATE, AND REACTIVE COMPOSITION CONTAINING SAME

TECHNICAL FIELD

The present invention relates to a reaction composition containing a urethane acrylate, and to a urethane acrylate for the same. In particular, the invention relates to a reaction composition which exhibits, after cured, high pencil hardness, scratch resistance, abrasion resistance, adhesiveness to substrate, transparency and contamination resistance, and to a urethane acrylate for the same.

BACKGROUND ART

A reaction composition containing a urethane acrylate can be made to have excellent characteristics of toughness, flexibility, scratch resistance, weather resistance, chemical resistance, and the like. Further, the composition has a characteristic of curing within a short period of time through heating or active energy ray irradiation, and is favorable for production of components for optical use, resist compositions, hard coat compositions, and ink compositions for inkjet.

In these latter days, in mobile electronic appliances such as notebook-size personal computers and mobile telephones, components having a fine patterned indented surface (for example, a key sheet) formed of a reactive resin composition on a sheet-like transparent plastic substrate, and housings with high-quality design are used in some cases and high pencil hardness and scratch resistance are required therefor. Consequently, attention has become paid to reactive compositions containing a urethane acrylate.

The cured product using the reactive composition described in Patent Literature 1 is excellent in scratch resistance, but in fact, the composition contains a solvent as described in Examples therein, and is therefore unfavorable for use in shaping applications. On the other hand, the cured product using the reactive composition described in Patent Literature 2 is disclosed to have excellent transparency and scratch resistance, but the composition uses a polyfunctional (meth)acryloyl group-containing compound such as 1,6-hexanediol diacrylate, trimethylolpropane triacrylate or dipentaerythritol hexaacrylate, and therefore, it is desired to reduce a curing shrinkage, to prevent an occurrence of a crack of the cured product and to improve an adhesiveness of the cured product to a substrate.

In Patent Literature 3, there is seen a description relating to a composition in which a urethane compound of a hexamethylene diisocyanate trimer with a monofunctional alcohol such as HEA, HPA, or HBA and a urethane compound with pentaerythritol triacrylate are produced, and thereto are incorporated a polyfunctional (meth)acrylate such as dipentaerythritol hexaacrylate, caprolactone-modified dipentaerythritol hexaacrylate, or dipentaerythritol-EO 12 mol adduct hexaacrylate. However, urethane acrylate as a base has high viscosity, and in order to prevent the physical properties from worsening, the composition naturally contains a polyfunctional alcohol derivative having high crystallinity and high viscosity. Therefore, there remain some problems in that a degree of lowering viscosity is low, and in case a monofunctional diluting monomer is added for lowering the viscosity, the physical properties of the cured product greatly worsen. Though the material is for shaping on a film, there is not made any evaluation in curing the composition on a film, relating to film deformation such as curling behavior, or curing shrinkage of the resin.

Not limited to the above-mentioned patent literatures, in a (meth)acrylate of a polyfunctional alcohol such as typically glycerin, diglycerin, trimethylolpropane, ditrimethylolpropane, pentaerythritol, dipentaerythritol, tripentaerythritol, tris(2-hydroxyethyl) isocyanurate, or sorbitol, an urethane acrylate compound reacted with an isocyanate with intentionally making a hydroxyl group remaining therein is incorporated in some cases in order to make a reactive composition to have high pencil hardness, scratch resistance, abrasion resistance, adhesiveness to substrate, transparency and weather resistance, which the present invention intend to have. However, as a whole, these urethane acrylate compounds have a high viscosity, and therefore have a problem of adhesiveness reduction owing to curing shrinkage and the same problems as in Patent Literature 3.

PRIOR ART LITERATURES

Patent Literatures

Patent Literature 1: JP-A-2005-15621
Patent Literature 2: JP-A-2004-338214
Patent Literature 3: JP-A-2009-040955

SUMMARY OF INVENTION

Problem that Invention is to Solve

The present invention has been made in consideration to the above, and its object is to provide a urethane acrylate to be obtained from a polyfunctional (meth)acrylate and a reactive composition containing the same, which solve the problems that the handleability of the reactive composition worsens and the curing shrinkage rate increases owing to the reason that the polyfunctional (meth)acrylate or a urethane acrylate thereof incorporated in the reactive composition has high crystallinity or high viscosity, and improve a curability and a surface hardness.

Means for Solving Problems

The present inventors have assiduously studied for the purpose of solving the above-mentioned problems and, as a result, have found that a urethane acrylate using a (meth)acrylate having a specific structure mentioned below, as derived from an alkylene oxide-modified dipentaerythritol, has excellent photosensitivity, low crystallinity, low viscosity and low curing shrinkage behavior and the cured product thereof has high hardness, as compared with a case using a (meth)acrylate derived from a polyfunctional alcohol such as typically diglycerin, glycerin, tripentaerythritol, dipentaerythritol, pentaerythritol, ditrimethylolpropane, or trimethylolpropane, and they have completed the present invention.

That is, the urethane acrylate of the present invention is one containing a reaction product of an alkylene oxide-modified dipentaerythritol (meth)acrylate having a structure represented by the following general formulae (I) and (II), and a polyisocyanate. The reactive composition of the present invention is one containing such the urethane acrylate.

[Chem. 1]

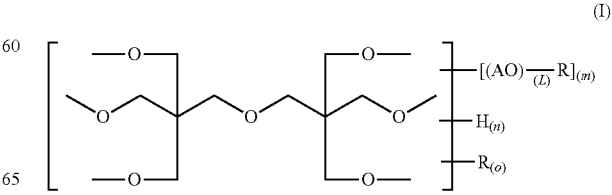

[Chem. 2]

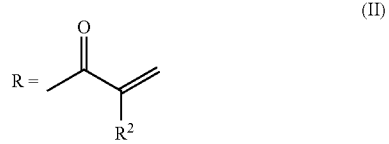

(II)

In the general formula (I), R represents a substituent represented by the general formula (II), AO indicates one or two or more selected from alkylene oxide units represented by —$CH_2CH_2O$—, —$CH_2CH(CH_3)O$—, —$CH_2CH_2CH_2CH_2O$— or —$CH_2CH(C_2H_5)O$—, a mean value of L indicating a mean degree of polymerization of added alkylene oxides is more than 0 and 5 or less, a mean value of m is more than 0 and 6 or less, a mean value of n is 0 or more and less than 6, a mean value of o is 0 or more and 6 or less, and a total of m, n and o is 6. In the general formula (II), $R^2$ represents a hydrogen atom or a methyl group.

Advantageous Effects of Invention

The urethane acrylate compound of the present invention has excellent photosensitivity, low crystallinity, low viscosity and low curing shrinkage behavior, and the cured product thereof has high hardness, and therefore, the physical properties of the cured product can be maintained or can be improved while the viscosity of the composition is reduced more, as compared with already-existing reactive compositions containing, a (meth)acrylate derived from a polyfunctional alcohol such as typically dipentaerythritol, pentaerythritol, ditrimethylolpropane, or trimethylolpropane, or an urethane compound thereof.

Owing to the above-mentioned characteristics, especially in non-solvent-based reactive compositions, a content of a monofunctional monomer to be added for viscosity reduction or for viscosity adjustment can be reduced or the addition may be omitted, and therefore the concentration of the (meth) acryloyl group that is a polymerizing functional group in the reactive composition can be increased.

Accordingly, it becomes possible to produce a cured product having improved curability, or that is, having a high crosslinking density, and therefore, in addition to the mechanical characteristics such as scratch resistance, contamination resistance, solvent resistance and heat resistance can be improved, and consequently, as its use, it can be favorably used for thermal recording media, optical discs, optical sheets, inks for inkjet, printing inks no using dampening water (inks for flexographic printing, inks for screen printing, or the like), optical fibers, and the like. On the other hand, in solvent-based including water-based reactive compositions, improvement of curability, improvement of adhesiveness to substrate owing to reduction in curing shrinkage, prevention of adhesiveness reduction in a heat-resistant test owing to the small content of the remaining double bond in the cured coating film to retard crosslinking under heat, improvement of weather resistance and light resistance, and the like can be realized.

Consequently, the urethane acrylate composition and the reactive composition of the present invention can be said to be materials having extreme superiority in use for reactive compositions for coating such as hard coat, reactive compositions for inks such as inkjet printing, reactive compositions for resists such as color resists, film coating, and the like.

In addition, though the compound and the reactive composition of the present invention can exhibit the above-mentioned characteristics even when used alone, they can still exhibit such characteristics even when used as combined with any already-existing reactive composition, for example, an alkylene oxide-unmodified polyfunctional (meth)acrylate such as an acrylate of dipentaerythritol, and therefore can be also used as additives.

MODE FOR CARRYING OUT INVENTION

<Alkylene Oxide-Modified Dipentaerythritol (Meth)acrylate>

An active hydrogen (hydroxyl group)-containing acrylate compound to be used in obtaining the urethane acrylate of the present invention has a structure represented by the above-mentioned general formulae (I) and (II). In the formula (I), AO indicates an alkylene oxide unit represented by —$CH_2CH_2O$—, —$CH_2CH(CH_3)O$—, —$CH_2CH_2CH_2CH_2O$— or —$CH_2CH(C_2H_5)O$—. Specifically, it indicates any of an ethylene oxide unit, a propylene oxide unit and a butylene oxide unit, and above all, preferred is the ethylene oxide unit from the viewpoint of the viscosity, the photosensitivity and the polymerization degree. These alkylene oxide units may exist as one alone or two or more types combined.

A mean value of L indicating a mean degree of polymerization of alkylene oxides is more than 0 and 5 or less, preferably more than 0 and 2 or less. A mean value of m is more than 0 and 6 or less, preferably 2 or more and 6 or less. A mean value of n indicating the number of the remaining hydroxyl groups is 0 or more and less than 6, preferably 1 or more and 2 or less. A mean value of o is 0 or more and 6 or less, preferably 0 or more and 4 or less. A total of these m, n and o is 6. In use for hard coating or the like, a mean added molar number of alkylene oxides (especially ethylene oxide) per one molecule of dipentaerythritol is preferably 2 or more and 5 or less, more preferably 3 or more and 5 or less.

R represents a (meth)acryloyl group represented by the general formula (II), and $R^2$ in the general formula (II) is a hydrogen atom or a methyl group.

Specifically, the hydroxyl group-containing acrylate compound for use in the present invention has a structure in which a part or all of six hydroxyl groups of dipentaerythritol are converted into (meth)acrylic acid ester groups represented by the general formula (II) via spacers of ethylene oxide, propylene oxide or butylene oxide, or plural types of these. In this, one or two hydroxyl groups not having a (meth)acrylic acid ester group have a form reactable with isocyanates.

<Production Method for Alkylene Oxide-Modified Dipentaerythritol (Meth)acrylate>

The alkylene oxide-modified polyfunctional (meth)acrylate in the present invention may be produced, for example, according to the method mentioned below, but the production route is not specifically limited and any production method is employable.

The alkylene oxide modification method using dipentaerythritol as a source material may be selected in any desired manner. As a general method, there is mentioned a method of using an alkylene oxide such as ethylene oxide, propylene oxide, butylene oxide or the like and, in addition thereto, there are also mentioned a method of using a cyclic carbonate such as ethylene carbonate, propylene carbonate, butylene carbonate or the like, and a method of using ethylene chlorohydrin.

In the production method to be mentioned below, the (meth)acrylic acid compound that is used as a source material for the urethane acrylate of the present invention has high polymerizability, and therefore during production or during storage of products, a polymerization inhibitor may be suitably used for preventing the polymerization from proceeding. The polymerization inhibitor includes hydroquinones such as p-benzoquinone, hydroquinone, hydroquinone monomethyl ether, and 2,5-diphenyl-parabenzoquinone, N-oxy radicals such as tetramethylpiperidinyl-N-oxy radical (TEMPO), substituted catechols such as t-butylcatechol, amines such as phenothiazine, diphenylamine, and phenyl-β-naphthylamine, cupferron, nitrosobenzene, picric acid, molecular oxygen, sulfur, copper(II) chloride, and the like. Of those, preferred are hydroquinones, phenothiazine and N-oxy radicals from the viewpoint of the general versatility and the polymerization inhibiting effect.

Regarding an amount of the polymerization inhibitor to be added, relative to the intended compound represented by the general formula (I), a lower limit is about 10 ppm or more preferably 30 ppm or more, and an upper limit is generally 5000 ppm or less, preferably 1000 ppm or less. In case the amount is too small, then a sufficient polymerization inhibiting effect could not be expressed and there is a risk of progression of polymerization during production and during storage of products, and in case too large, then on the contrary, there is a risk of inhibiting the curing and polymerization reaction. Consequently, in the compound of the present invention alone or in the polymerizable resin composition thereof, there may be a risk of occurring reduction in the photosensitivity, crosslinking failure of cured products, degradation of the physical properties such as the mechanical strength, or the like, and it is not preferred.

An ordinary method for (meth)acrylic acid ester group introduction in producing the hydroxyl group-containing acrylate compound for use in the present invention includes an interesterification method that uses a (meth)acrylic acid ester corresponding to the intended structure such as methyl acrylate or methyl methacrylate, an acid chloride method that uses a (meth)acrylic acid chloride, a method using a condensing agent such as N,N'-dicyclohexylcarbodiimide, 2-chloro-1,3-dimethylimidazolium chloride, propanephosphonic acid anhydride, carbonyldiimidazole (CDI), or WSCD (water-soluble carbodiimide), a dehydration esterification method of azeotropic dehydration with (meth)acrylic acid in the presence of an acid catalyst, and the like. For typical esterification of an alkylene oxide-modified dipentaerythritol, possible conditions in production are mentioned below.

The reaction can be carried out by reacting (meth)acrylic acid and an alkylene oxide-modified dipentaerythritol in the presence of an acid catalyst while the formed water is distilled away. The acid to be used is not specifically limited, and may be any acid usable in ordinary esterification. For example, there are mentioned inorganic acids such as sulfuric acid and hydrochloric acid, organic sulfonic acids such as p-toluenesulfonic acid, methanesulfonic acid, and camphorsulfonic acid, acid-type ion-exchange resins, Lewis acids such as boron fluoride/ether complex, water-soluble Lewis acids such as lanthanide triflate, and the like. These acids can be used as one alone or as two or more types of arbitrary acids combined.

Regarding the amount of the acid to be used, relative to alkylene oxide-modified dipentaerythritol as a substrate, a lower limit is 0.1 molar equivalent or more, preferably 0.5 molar equivalent or more. On the other hand, an upper limit is not specifically limited, but is generally 20 molar equivalents or less, preferably 10 molar equivalents or less. In the case the amount of the acid catalyst is too small, such is unfavorable since the reaction progress would be slow or the reaction may stop, and in case too large, some problems such as product discoloration or catalyst residue and some unfavorable side reaction such as production of Michael adducts tend to occur.

The reaction may be carried out in solvent-based system or non-solvent-based system, but in view of side product formation and of handleability in the process, solvent-based system is preferred. In case the solvent is used, the solvent to be used is not specifically limited, but preferably used is an aromatic hydrocarbon solvent such as toluene and xylene, an aliphatic hydrocarbon solvent such as hexane and heptane, an ether solvent such as diethyl ether, tetrahydrofuran, monoethylene glycol dimethyl ether, and diethylene glycol dimethyl ether, a halogen solvent such as methylene chloride, chloroform, and carbon tetrachloride, and the like. These solvents may be used as one alone or as plurality of arbitrary solvents combined.

In case the solvent is used, the amount thereof may be so adjusted that the concentration of a source material, alkylene oxide-modified dipentaerythritol therein could be generally 1% by mass or more, preferably 20% by mass or more. An upper limit is not specifically limited, but is generally 80% by mass or less, preferably 70% by mass or less. The reaction is carried out generally at a temperature of the boiling point of the solvent used or higher while the formed water is distilled away. However, in case where the reaction using the above-mentioned (meth)acrylic acid chloride or the condensing agent is carried out, the reaction may be carried out at a temperature of the boiling point of the solvent or lower or with cooling with ice. The reaction time may be selected in any desired manner. By measuring the amount of the formed water and the acid value inside the system, the end point of the reaction can be recognized.

Regarding the reaction time, a lower limit is generally 30 minutes or more, preferably 60 minutes or more, and an upper limit is, though not specifically limited, generally 20 hours or less, preferably 10 hours or less.

<Purification Method>

The compound produced through the above-mentioned reaction and represented by the general formula (I) may be purified in any purification method heretofore employed, with no specific limitation thereon. For example, there may be mentioned a distillation method, a recrystallization method, an extraction washing method, an adsorption treatment method, and the like. In case distillation is performed, the mode thereof may be arbitrary selected from single distillation, precision distillation, thin film distillation, molecular distillation, and the like.

<Method for Storage of (Meth)acrylic Acid Ester Monomer>

The (meth)acrylic acid ester monomer in the present invention is polymerizable and is therefore desired to be stored in a cold and dark place. For preventing polymerization, the above-mentioned polymerization inhibitor may be used in the above-mentioned amount for storage.

<Production of Urethane Acrylate from Alkylene Oxide-Modified Dipentaerythritol (Meth)acrylate and Polyisocyanate>

The urethane acrylate of the present invention contains a reaction product of the above-mentioned alkylene oxide-modified dipentaerythritol (meth)acrylate with a polyisocyanate to be mentioned below. The urethane acrylate of the present invention may also contain a reaction product of the above-mentioned alkylene oxide-modified polyfunctional (meth)acrylate and a hydroxyl group-containing (meth)acrylate to be mentioned below, with a polyisocyanate to be mentioned below. Typically, the polyisocyanate may have a molecular weight of 1000 or less, and has from 2 to 5 isocyanate groups, especially from 2 to 3 isocyanate groups in each molecule. The polyisocyanate for use in the present invention is especially an organic polyisocyanate having a skeleton of an organic compound. For use in hard coating or the like, preferred is a polyisocyanate having an aliphatic skeleton.

The polyisocyanate includes tolylene diisocyanate, xylylene diisocyanate, diphenylmethane diisocyanate, isophorone diisocyanate, hexamethylene diisocyanate, dicyclohexylmethane diisocyanate, methylcyclohexane diisocyanate, norbornene diisocyanate, toluylene diisocyanate, hydrogenated xylylene diisocyanate, naphthalene diisocyanate, tetramethylxylene diisocyanate, dimer acid diisocyanate, and trimethylhexamethylene diisocyanate, and multimers of isocyanates, such as trimer of trimethylhexamethylene diisocyanate.

Examples of the hydroxyl group-containing alkyl (meth) acrylate to be reacted with the polyisocyanate along with the above-mentioned alkylene oxide-modified dipentaerythritol (meth)acrylate include hydroxyl group-containing (meth) acrylates such as 2-hydroxyethyl (meth)acrylate, 2-hydroxypropyl (meth)acrylate, 2-hydroxybutyl (meth)acrylate, 4-hydroxybutyl (meth)acrylate, 6-hydroxyhexyl (meth)acrylate, and pentaerythritol tri(meth)acrylate, their caprolactone-modified derivatives alkyl oxide-modified derivatives, and the like. Also employable here are addition reaction products of a monoepoxy compound such as butyl glycidyl ether, 2-ethylhexyl glycidyl ether, glycidyl (meth)acrylate or the like with a (meth)acrylic acid monomer. Further employable are those produced by introducing a hydroxyl group into the above-mentioned alkylene oxide-modified dipentaerythritol (meth)acrylate.

The addition reaction of the above-mentioned isocyanate component with the acrylate compound may be carried out in accordance with various heretofore-known methods. For example, it can be carried out by heating a mixture of an isocyanate component and a catalyst such as dibutyltin dilaurate at 30 to 90° C., dropwise adding an acrylate compound thereto, and performing a reaction for 6 to 12 hours.

<Reactive Composition>

The reactive composition of the present invention contains the above-mentioned urethane acrylate.

The polymerization and curing of the reactive composition of the present invention may be carried out according to generally-known methods, which are not specifically limited. For example, a method such as a method of polymerization in the presence of a radical initiator, a method of polymerization with an active energy ray using electron beams or UV rays from a light source such as LED and high-pressure mercury lamp in the presence of a polymerization initiator, a thermal polymerization method, an anionic polymerization, or an addition polymerization can be employed as one alone or as combined.

The polymerization initiator is not specifically limited. As a photopolymerization initiator, for example, usable are aromatic ketones such as benzophenone, aromatic compounds such as anthracene and α-chloromethylnaphthalene, sulfur compounds such as diphenyl sulfide and thiocarbamate.

As a radical polymerization initiator, for example, usable are organic peroxides such as benzoyl peroxide, methylcyclohexanone peroxide, cumene hydroperoxide, diisopropylbenzene peroxide, di-t-butyl peroxide, t-butylperoxy benzoate, diisopropylperoxy carbonate, and t-butylperoxyisopropyl monocarbonate, azo compounds such as 2,2'-azobisisobutyronitrile (AIBN). If desired, these photopolymerization initiator and radical polymerization initiator may be combined for use.

As the polymerization initiator in the case of active energy rays such as UV rays, for example, there are mentioned acetophenone, acetophenone benzyl ketal, 1-hydroxycyclohexylphenyl ketone, 2,2-dimethoxy-1,2-diphenylethan-1-one, xanthone, fluorenone, benzaldehyde, fluorene, anthraquinone, triphenylamine, carbazole, 3-methylacetophenone, 4-chlorobenzophenone, 4,4'-dimethoxybenzophenone, 4,4'-diaminobenzophenone, benzoin propyl ether, benzoin ethyl ether, benzyldimethyl ketal, 1-(4-isopropylphenyl)-2-hydroxy-2-methylpropan-1-one, 2-hydroxy-2-methyl-1-phenylpropan-1-one, thioxanthone, diethylthioxanthone, 2-isopropylthioxanthone, 2-chlorothioxanthone, 2-methyl-1-[4-(methylthio)phenyl]-2-morpholino-propan-1-one, 2-benzyl-2-dimethylamino-1-(4-morpholinophenyl)-butanone-1,4-(2-hydroxyethoxyl)phenyl-(2-hydroxy-2-propyl)ketone, 2,4,6-trimethylbenzoyldiphenylphosphine oxide, bis(2,6-dimethoxybenzoyl)-2,4,4-trimethylpentylphosphine oxide, oligo(2-hydroxy-2-methyl-1-(4-(1-methylvinyl)phenyl)propanone), and the like.

As commercial products of the polymerization initiator in the case of active energy rays, for example, there are mentioned ones manufactured by Ciba Specialty Chemicals, trade names: Irgacure 184, 369, 651, 500, 819, 907, 784, 2959, CGI1700, CGI1750, CGI1850, CG24-61, Dalocure 1116, and 1173, one manufactured by BASF, trade name: Lucirin TPO, one manufactured by UCB, trade name: Ebecryl P36, ones manufactured by Fratelli-Lamberti, trade names: Ezacure KIP150, KIP65LT, KIP100F, KT37, KT55, KT046, and KIP75/B, and the like.

The amount to be used of the above-mentioned photopolymerization initiator, radical polymerization initiator and polymerization initiator in the case of active energy rays may be selected in accordance with known polymerization reaction. For example, in general, the amount of the radical polymerization initiator to be used is suitably from 0.0001 to 10 parts by weight, preferably from 0.001 to 5 parts by weight relative to the compound represented by the general formula (I) of the present invention. Regarding the reaction temperature, a lower limit is generally 0° C. or higher, preferably 10° C. or higher, and on the other hand, an upper limit is generally 200° C. or lower, preferably 100° C. or lower.

EXAMPLES

The present invention is described in more detail with reference to the following Examples. Within a range overstepping the scope and the spirit thereof, the present invention is not whatsoever limited by the following Examples. Unless otherwise specifically indicated, "%" is mass %, and "part" is by mass.

<Conditions for Liquid Chromatography Mass Spectrometry (Hereinafter Abbreviated as LC-MS)>

In Examples and Comparative Examples, the conditions for LC-MS were as mentioned below.

[LC Part] Manufactured by Agilent Technologies, 1100 Series,

Column: Inertsil ODS-2 (4.6 mmφ×250 mm, 5 μm),

Eluent: water 80.0%-30 min→0.0%, methanol 20.0%-30 min→100.0%,

Column temperature: 40° C.,

Flow rate: 1 mL/min, Injection amount: 5 μL (200 ppm methanol solution),

Detector: UV, RI.

[MS Part] JMS T100LP (manufactured by JEOL)

Ring lens voltage: 10V, Ionization method: APCI+, Solvent removal chamber temperature: 350° C., Needle voltage: 2500 V, Orifice 1 temperature: 80° C., Orifice 1 voltage: 60 V, Ion guide peak-to-peak voltage: 1000 V, Orifice 2 voltage: 5 V.

<Condition for Measurement of Hydroxyl Value>

Acetic acid and pyridine were mixed in a ratio 1:9 by weight to prepare an acetylation reagent. A sample was weighed and put in a flask, the acetylation reagent was added thereto and heated at 80° C. for 2 hours. After the reaction, titration was performed with an aqueous 1 mol/L potassium hydroxide solution using phenolphthalein as an indicator.

<NMR Analysis>

For the results of NMR analysis, attribution of each peak is indicated by the number ((1) to (3)) shown in the following formula.

[Chem. 3]

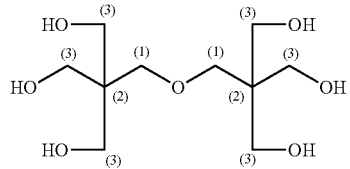

Synthesis Example 1

Synthesis of Dipentaerythritol 2EO Adduct Acrylate

In an autoclave having a volume of 1 and equipped with a stirrer were put 254 g (1.0 mol) of dipentaerythritol (manufactured by Koei Chemical Company, OH value 1324), 127 g of toluene and 0.3 g of KOH, and heated up to 90° C. and stirred to give a slurry liquid. Next, this was heated up to 130° C., and 132 g (3 mol) of ethylene oxide was gradually introduced into the autoclave and reacted. Along with the introduction of the ethylene oxide, the inner temperature of the autoclave was increased. This was cooled as needed so as to keep the reaction temperature at 140° C. or less. After the reaction, this was depressurized at 10 mmHg or less of mercury column at 140° C. to thereby remove the excessive ethylene oxide and the side product, ethylene glycol polymer. Subsequently, this was neutralized with acetic acid to have an adjusted pH of from 6 to 7. The OH value of the resultant dipentaerythritol 2EO adduct (with 2 moles on average of ethylene oxide added—the same shall apply hereinunder) was 982.

Into a four-neck glass flask were put 343 g (1 mol) of the resultant ethylene glycol-modified dipentaerythritol (OH value 982), 367 g (5.1 mol) of acrylic acid, 35 g of paratoluenesulfonic acid, 900 g of toluene, and 0.9 g of hydroquinone, and reacted under heat while an air blow was introduced thereinto. Water formed through the reaction was removed out of the system as needed through azeotrophy with toluene. The reaction temperature was from 100 to 110° C., and the amount of the reaction water that had been removed out of the system by the end of the reaction was 95 g. After the reaction, wash with alkali and wash with water were performed, the upper toluene layer was separated, and toluene was distilled away under reduced pressure to give 538 g (yield 87%) of a hydroxyl group-containing dipentaerythritol 2EO adduct acrylate represented by the general formula (I).

This was analyzed for the measurement of the hydroxyl value thereof, and analyzed through $^1$H-NMR, $^{13}$C-NMR, HPLC, LC-MS and hydroxyl value measurement, and as a result, it was clarified that it is a hydroxyl group-containing dipentaerythritol 2EO adduct acrylate. The results of the NMR analyses and the LC-MS analysis are shown below, and the peak attribution in NMR is expressed by the above-mentioned number.

<$^{13}$C-NMR Analysis (400 MHz) of 2EO Adduct Acrylate, in CDCl$_3$>

45 ppm: derived from (2), 60 ppm: derived from (3), 61 to 63 ppm: derived from ethylene oxide-added (3), 68 to 73 ppm: derived from ethylene oxide added to (3), 77 to 79 ppm: derived from heavy chloroform, 128 to 131 ppm: derived from ester-bonded acrylic acid, 165 to 167 ppm: ester bond part.

<$^1$H-NMR Analysis (400 MHz) of 2EO Adduct Acrylate, in CDCl$_3$>

3.3 to 4.1 ppm (16H): derived from (1) and (3), 3.6 to 4.4 ppm (8H): derived from ethylene oxide added to OH at (3), 5.7 to 6.4 ppm (18H): derived from double bond of acrylic acid ester, 7.3 ppm: derived from heavy chloroform.

<LC-MS Analysis of 2EO Adduct Acrylate>

8.8 to 11.5 min: ethylene oxide polymer diacrylate, 14 to 16 min: dipentaerythritol ethylene oxide-modified monoacrylate, 16 to 20 min: dipentaerythritol ethylene oxide-modified hexaacrylate.

<Hydroxyl Value of 2EO Adduct Acrylate>

Relative to the calculated hydroxyl value of 54 mg KOH/g of dipentaerythritol 2EO adduct dipentaacrylate monoalcohol, the measured value was 49 mg KOH/g.

Synthesis Example 2

Synthesis of Dipentaerythritol 4EO Adduct Acrylate

In an autoclave having a volume of 1 L and equipped with a stirrer were put 254 g (1.0 mol) of dipentaerythritol (manufactured by Koei Chemical Company, OH value 1324), 127 g of toluene and 0.3 g of KOH, and heated up to 90° C. and stirred to give a slurry liquid. Next, this was heated up to 130° C., and 220 g (5 mol) of ethylene oxide was gradually introduced into the autoclave and reacted. Along with the introduction of ethylene oxide, the inner temperature of the autoclave was increased. This was cooled as needed so as to keep the reaction temperature at 140° C. or less. After the reaction, this was depressurized at 10 mmHg or less of mercury column at 140° C. to thereby remove the excessive ethylene oxide and the side product, ethylene glycol polymer. Subsequently, this was neutralized with acetic acid to have an adjusted pH of from 6 to 7. The OH value of the resultant dipentaerythritol 4EO adduct was 765.

Into a four-neck glass flask were put 440 g (1 mol) of the resultant ethylene glycol-modified dipentaerythritol (OH value 765), 382 g (5.3 mol) of acrylic acid, 41 g of paratoluenesulfonic acid, 900 g of toluene, and 1 g of hydroquinone, and reacted under heat while an air blow was introduced thereinto. Water formed through the reaction was removed out of the system as needed through azeotrophy with toluene. The reaction temperature was from 100 to 110° C., and the amount of the reaction water that had been removed out of the system by the end of the reaction was 99 g. After the reaction, wash with alkali and wash with water were performed, the upper toluene layer was separated, and toluene was distilled away under reduced pressure to give 610 g (yield 86%) of a hydroxyl group-containing dipentaerythritol 4EO adduct acrylate represented by the general formula (I).

This was analyzed for the measurement of the hydroxyl value thereof, and analyzed through $^1$H-NMR, $^{13}$C-NMR, HPLC, LC-MS and hydroxyl value measurement, and as a result, it was clarified that it is a hydroxyl group-containing dipentaerythritol 4EO adduct acrylate. The results of the NMR analyses and the LC-MS analysis are shown below, and the peak attribution in NMR is expressed by the above-mentioned number.

<$^{13}$C-NMR Analysis (400 MHz) of 4EO Adduct Acrylate, in CDCl$_3$>

45 ppm: derived from (2), 60 ppm: derived from (3), 61 to 63 ppm: derived from ethylene oxide-added (3), 68 to 73 ppm: derived from ethylene oxide added to (3), 77 to 79 ppm: derived from heavy chloroform, 128 to 131 ppm: derived from ester-bonded acrylic acid, 165 to 167 ppm: ester bond part.

<$^{1}$H-NMR Analysis (400 MHz) of 4EO Adduct Acrylate, in CDCl$_3$>

3.3 to 4.1 ppm (16H): derived from (1) and (3), 3.6 to 4.4 ppm (16H): derived from ethylene oxide added to OH at (3), 5.7 to 6.4 ppm (18H): derived from double bond of acrylic acid ester, 7.3 ppm: derived from heavy chloroform.

<LC-MS Analysis of 4EO Adduct Acrylate>

8.8 to 11.5 min: ethylene oxide polymer diacrylate, 14 to 16 min: dipentaerythritol ethylene oxide-modified monoacrylate, 16 to 20 min: dipentaerythritol ethylene oxide-modified hexaacrylate.

<Hydroxyl Value of 4EO Adduct Acrylate>

Relative to the calculated hydroxyl value of 54 mg KOH/g of dipentaerythritol 4EO adduct dipentaacrylate monoalcohol, the measured value was 51 mg KOH/g.

Synthesis Example 3

Synthesis of Dipentaerythritol 6EO Adduct Acrylate

In an autoclave having a volume of 1 L and equipped with a stirrer were put 254 g (1.0 mol) of dipentaerythritol (manufactured by Koei Chemical Company, OH value 1324), 36 g of distilled water and 0.3 g of KOH, and heated up to 90° C. and stirred to give a slurry liquid. Next, this was heated up to 130° C., and 352 g (8 mol) of ethylene oxide was gradually introduced into the autoclave and reacted. Along with the introduction of ethylene oxide, the inner temperature of the autoclave was increased. This was cooled as needed so as to keep the reaction temperature at 140° C. or less. After the reaction, this was depressurized at 10 mmHg or less of mercury column at 140° C. to thereby remove the excessive ethylene oxide and the side product, ethylene glycol polymer. Subsequently, this was neutralized with acetic acid to have an adjusted pH of from 6 to 7. The OH value of the resultant dipentaerythritol 6EO adduct was 646.

Into a four-neck glass flask were put 521 g (1 mol) of the resultant ethylene glycol-modified dipentaerythritol (OH value 646), 389 g (5.4 mol) of acrylic acid, 45 g of paratoluenesulfonic acid, 900 g of toluene, and 1.1 g of hydroquinone, and reacted under heat while an air blow was introduced thereinto. Water formed through the reaction was removed out of the system as needed through azeotrophy with toluene. The reaction temperature was from 100 to 110° C., and the amount of the reaction water that had been removed out of the system by the end of the reaction was 113 g. After the reaction, wash with alkali and wash with water were performed, the upper toluene layer was separated, and toluene was distilled away under reduced pressure to give 669 g (yield 83%) of a hydroxyl group-containing dipentaerythritol 6EO adduct acrylate represented by the general formula (I).

This was analyzed for the measurement of the hydroxyl value thereof, and analyzed through $^1$H-NMR, $^{13}$C-NMR, HPLC and LC-MS, and as a result, it was clarified that it is a hydroxyl group-containing dipentaerythritol 6EO adduct acrylate. The results of the NMR analyses, the LC-MS analysis and the hydroxyl value measurement are shown below, and the peak attribution in NMR is expressed by the above-mentioned number.

<$^{13}$C-NMR Analysis (400 MHz) of 6EO Adduct Acrylate, in CDCl$_3$>

45 ppm: derived from (2), 60 ppm: derived from (3), 61 to 63 ppm: derived from ethylene oxide-added (3), 68 to 73 ppm: derived from ethylene oxide added to (3), 77 to 79 ppm: derived from heavy chloroform, 128 to 131 ppm: derived from ester-bonded acrylic acid, 165 to 167 ppm: ester bond part.

<$^1$H-NMR Analysis (400 MHz) of 6EO Adduct Acrylate, in CDCl$_3$>

3.3 to 4.1 ppm (16H): derived from (1) and (3), 3.6 to 4.4 ppm (24H): derived from ethylene oxide added to OH at (3), 5.7 to 6.4 ppm (18H): derived from double bond of acrylic acid ester, 7.3 ppm: derived from heavy chloroform.

<LC-MS Analysis of 6EO Adduct Acrylate>

8.8 to 11.5 min: ethylene oxide polymer diacrylate, 14 to 16 min: dipentaerythritol ethylene oxide-modified monoacrylate, 16 to 20 min: dipentaerythritol ethylene oxide-modified hexaacrylate.

<Hydroxyl Value of 6EO Adduct Acrylate>

Relative to the calculated hydroxyl value of 54 mg KOH/g of dipentaerythritol 6EO adduct dipentaacrylate monoalcohol, the measured value was 50 mg KOH/g.

Example 1

Reaction of Dipentaerythritol 2EO Adduct Acrylate with Isophorone Diisocyanate

Into a 2-liter separable flask were put 1236 parts (2 mol) of the dipentaerythritol 2EO adduct acrylate obtained in Synthesis Example 1, 222 parts (1 mol) of isophorone diisocyanate (manufactured by Sumitomo Bayer, trade name: Desmodur I) and 0.4 parts of hydroquinone monomethyl ether (manufactured by Kawaguchi Chemical Industry, trade name: MQ). With stirring, air was introduced into the liquid through a glass tube, and the liquid temperature was made to be 70° C. Thereto was added 0.3 parts of dibutyltin dilaurate (manufactured by Asahi Denka Industry, trade name: Adekastab BT-11) and while the reaction temperature was adjusted to be between 70 and 80° C., reaction was performed for 6 hours to give a urethane acrylate of isophorone diisocyanate and dipentaerythritol 2EO adduct.

Example 2

Reaction of Dipentaerythritol 4EO Adduct Acrylate with Isophorone Diisocyanate

Into a 2-liter separable flask were put 1418 parts (2 mol) of the dipentaerythritol 4EO adduct acrylate obtained in Synthesis Example 2, 222 parts (1 mol) of isophorone diisocyanate and 0.45 parts of hydroquinone monomethyl ether. With stirring, air was introduced into the liquid through a glass tube, and the liquid temperature was made to be 70° C. Thereto was added 0.34 parts of dibutyltin dilaurate and while the reaction temperature was adjusted to be between 70 and 80° C., reaction was performed for 6 hours to give a urethane acrylate of isophorone diisocyanate and dipentaerythritol 4EO adduct.

Example 3

Reaction of Dipentaerythritol 6EO Adduct Acrylate with Isophorone Diisocyanate Into a 2-liter separable flask were put 1612 parts (2 mol) of the dipentaerythritol 6EO adduct acrylate obtained in Synthesis Example 3, 222 parts (1 mol) of isophorone diisocyanate and 0.5 parts of hydroquinone monomethyl ether. With stirring, air was introduced into the liquid through a glass tube, and the liquid temperature was made to be 70° C. Thereto was added 0.38 parts of dibutyltin dilaurate and while the reaction temperature was adjusted to be between 70 and 80° C., reaction was performed for 6 hours to give a urethane acrylate of isophorone diisocyanate and dipentaerythritol 6EO adduct.

Example 4

Reaction of Dipentaerythritol 2EO Adduct Acrylate with Hexamethylene Diisocyanate Trimer Into a 3-liter separable flask were put 1854 parts (3 mol) of the dipentaerythritol 2EO adduct acrylate obtained in Synthesis Example 1, 540 parts (1 mol) of hexamethylene diisocyanate trimer and 0.48 parts of hydroquinone monomethyl ether. With stirring, air was introduced into the liquid through a glass tube, and the liquid temperature was made to be 70° C. Thereto was added 0.48 parts of dibutyltin dilaurate and while the reaction temperature was adjusted to be between 70 and 80° C., reaction was performed for 6 hours to give a urethane acrylate of hexamethylene diisocyanate trimer and dipentaerythritol 2EO adduct.

Example 5

Reaction of Dipentaerythritol 4EO Adduct Acrylate with Hexamethylene Diisocyanate Trimer Into a 3-liter separable flask were put 2127 parts (3 mol) of the dipentaerythritol 4EO adduct acrylate obtained in Synthesis Example 2, 540 parts (1 mol) of hexamethylene diisocyanate trimer and 0.53 parts of hydroquinone monomethyl ether. With stirring, air was introduced into the liquid through a glass tube, and the liquid temperature was made to be 70° C. Thereto was added 0.53 parts of dibutyltin dilaurate and while the reaction temperature was adjusted to be between 70 and 80° C., reaction was performed for 7 hours to give a urethane acrylate of hexamethylene diisocyanate trimer and dipentaerythritol 4EO adduct.

Example 6

Reaction of Dipentaerythritol 6EO Adduct Acrylate with Hexamethylene Diisocyanate Trimer Into a 3-liter separable flask were put 2418 parts (3 mol) of the dipentaerythritol 6EO adduct acrylate obtained in Synthesis Example 3, 540 parts (1 mol) of hexamethylene diisocyanate trimer and 0.59 parts of hydroquinone monomethyl ether. With stirring, air was introduced into the liquid through a glass tube, and the liquid temperature was made to be 70° C. Thereto was added 0.59 parts of dibutyltin dilaurate and while the reaction temperature was adjusted to be between 70 and 80° C., reaction was performed for 7 hours to give a urethane acrylate of hexamethylene diisocyanate trimer and dipentaerythritol 6EO adduct.

Comparative Example 1

Reaction of Pentaerythritol Triacrylate with Isophorone Diisocyanate

Into a 1-liter separable flask were put 667 parts (2 mol) of pentaerythritol triacrylate (manufactured by Nippon Kayaku, trade name: KAYARAD PET-30), 222 g (1 mol) of isophorone diisocyanate and 0.18 parts of hydroquinone monomethyl ether. With stirring, air was introduced into the liquid through a glass tube, and the liquid temperature was made to be 70° C. Thereto was added 0.18 parts of dibutyltin dilaurate and while the reaction temperature was adjusted to be between 70 and 80° C., reaction was performed for 6 hours to give a urethane acrylate of isophorone diisocyanate and pentaerythritol triacrylate.

Comparative Example 2

Reaction of Dipentaerythritol Acrylate with Isophorone Diisocyanate

Into a 3-liter separable flask were put 2248 parts (2 mol) of dipentaerythritol acrylate (manufactured by Nippon Kayaku, trade name: KAYARAD DPHA), 222 parts (1 mol) of isophorone diisocyanate and 0.49 parts of hydroquinone monomethyl ether. With stirring, air was introduced into the liquid through a glass tube, and the liquid temperature was made to be 70° C. Thereto was added 0.49 parts of dibutyltin dilaurate and while the reaction temperature was adjusted to be between 70 and 80° C., reaction was performed for 6 hours to give a urethane acrylate of isophorone diisocyanate and dipentaerythritol acrylate.

Comparative Example 3

Reaction of 2-Hydroxyethyl Acrylate with Isophorone Diisocyanate

Into a 1-liter separable flask were put 232 parts (2 mol) of 2-hydroxyethyl acrylate (manufactured by Nippon Shokubai, trade name: BHEA), 222 parts (1 mol) of isophorone diisocyanate and 0.09 parts of hydroquinone monomethyl ether. With stirring, air was introduced into the liquid through a glass tube, and the liquid temperature was made to be 70° C. Thereto was added 0.09 parts of dibutyltin dilaurate and while the reaction temperature was adjusted to be between 70 and 80° C., reaction was performed for 6 hours to give a urethane acrylate of isophorone diisocyanate and 2-hydroxyethyl acrylate.

Comparative Example 4

Reaction of 2-Hydroxyethyl Acrylate with Hexamethylene Diisocyanate Trimer

Into a 1-liter separable flask were put 348 parts (3 mol) of 2-hydroxyethyl acrylate, 540 parts (1 mol) of hexamethylene diisocyanate trimer (manufactured by Asahi Kasei Chemicals, trade name: Duranate TLA-100), and 0.18 parts of hydroquinone monomethyl ether. With stirring, air was introduced into the liquid through a glass tube, and the liquid temperature was made to be 70° C. Thereto was added 0.18 parts of dibutyltin dilaurate and while the reaction temperature was adjusted to be between 70 and 80° C., reaction was performed for 6 hours to give a urethane acrylate of hexamethylene diisocyanate trimer and 2-hydroxyethyl acrylate.

Comparative Example 5

Reaction of Dipentaerythritol Triacrylate with Hexamethylene Diisocyanate Trimer Into a 5-liter separable flask were put 3372 parts (3 mol) of dipentaerythritol triacrylate, 540 parts (1 mol) of hexamethylene diisocyanate trimer (manufactured by Asahi Kasei Chemicals, trade name: Duranate TLA-100), and 0.78 parts of hydroquinone monomethyl ether. With stirring, air was introduced into the liquid through a glass tube, and the liquid temperature was made to be 70° C. Thereto was added 0.78 parts of dibutyltin dilaurate and while the reaction temperature was adjusted to be between 70 and 80° C., reaction was performed for 6 hours to give a urethane acrylate of hexamethylene diisocyanate trimer and dipentaerythritol triacrylate.

Comparative Example 6

Reaction of Pentaerythritol Triacrylate with Hexamethylene Diisocyanate Trimer

Into a 2-liter separable flask were put 1001 parts (3 mol) of pentaerythritol triacrylate, 540 parts (1 mol) of hexamethylene diisocyanate trimer, and 0.31 parts of hydroquinone monomethyl ether. With stirring, air was introduced into the liquid through a glass tube, and the liquid temperature was made to be 70° C. Thereto was added 0.31 parts of dibutyltin dilaurate and while the reaction temperature was adjusted to be between 70 and 80° C., reaction was performed for 5 hours to give a urethane acrylate of hexamethylene diisocyanate trimer and pentaerythritol triacrylate.

[Viscosity]

Measured according to JIS K 5600-2-3.

[Photosensitivity]

50 parts by weight of the sample obtained in Examples 1 to 6 and Comparative Examples 1 to 6, 50 parts by weight of ethyl acetate, and 3 parts by weight, relative to the solid content, of Irgacure 184 manufactured by BASF as a photopolymerization initiator, were mixed and dissolved, and the resulting material was applied onto a glass substrate with a spin coater in a dry thickness of 5 μm, and then dried at 80° C. for solvent removal. Masked with a step tablet (25-stage, manufactured by Riston), the uncured product was cured with a parallel photoexposure device manufactured by Ushio (SX-UID501H UVQ) in a nitrogen atmosphere at an integrated illumination of 200 mj, and the number of tack-free stages in finger touch was counted.

[Adhesiveness]

The sample prepared in the same manner as the item of photosensitivity was cured by using a belt conveyor-type UV curing device equipped with a metal halide lamp at an integrated illumination of 200 mj/cm2, in which ABS, acrylic resin, PC or PET (the surface thereof treated for adhesion improvement) was used as the substrate. According to a cross-cut peeling test as stipulated in JIS-K5400, the number of the remaining cross cuts was counted to evaluate the adhesiveness.

[Pencil Hardness]

A cured film was formed according to the same method as in the item of photosensitivity, and the film hardness on ABS, PC, PET or acrylic resin was measured according to JIS K5600-5-4.

[Scratch Resistance]

A cured film was formed on a PET film (the surface thereof treated for adhesion improvement) according to the same method as in the item of photosensitivity, and a Taber abrasion test was performed. Using a CS-10F wear ring under 1-kg load, a haze after rotated for a predetermined times was measured with a haze meter (manufactured by Suga Test Instruments, HGM Model). The difference in the haze of the sample before and after the test was determined.

[Steel Wool Resistance]

A cured film was formed on a PET film (the surface thereof treated for adhesion improvement) according to the same method as in the item of photosensitivity, and rubbed 100 times with No. 00 steel wool under 3-kg load, whereupon the condition of the film was visually observed and evaluated according to the following criteria.

A: No scratch.
B: About 10 scratches were confirmed on the test piece.
C: Many scratches were confirmed.

[Curling Behavior]

A PET film cut into a square with a thickness of 150 μm and a side length of 6 cm was used as a substrate and a cured film was formed thereon according to the same method as in the item of photosensitivity. One point of the four corners of the film was fixed on a flat plane, the height of the remaining three points was measured, and the average value was determined to indicate curling behavior.

[Contamination Resistance]

A cured film was formed on a PET film (the surface thereof treated for adhesion improvement) according to the same method as in the item of photosensitivity. As a contaminant, oily ink, hair dye or shoe cream was applied on the cured film, left as such for 18 hours, and then wiped away with ethanol/cotton, whereupon the outward appearance was visually checked and evaluated according to the following criteria.

A: Not colored.
B: Colored a little.
C: Colored thickly.

[Foldability]

A cured film was formed on a PET film (the surface thereof treated for adhesion improvement) according to the same method as in the item of photosensitivity.

The formed film was wound around a column having a respective diameter in such a manner that the cured layer could be outside, and the diameter of the column when the film was cracked was recorded.

TABLE 1

| | Structure | Viscosity (mPas/ 25° C.) | Curling Behavior [mm] | Pencil Hardness | Foldability [mm] | Transmittance [%] | Scratch Resistance (haze difference) | Photo-sensitivity (x/25) |
|---|---|---|---|---|---|---|---|---|
| Ex. 1 | DPEA2-IPDI | 34 | 4 | 2H | 4 | 91 | 1.2 | 10 |
| Ex. 2 | DPEA4-IPDI | 13 | 2 | 2H | 1 | 90.8 | 0.9 | 14 |
| Ex. 3 | DPEA6-IPDI | 22 | 1 | H | 1 | 91.8 | 5.9 | 15 |

TABLE 1-continued

| | | | | | | | | |
|---|---|---|---|---|---|---|---|---|
| Ex. 4 | DPEA2-HMDI trimer | 85 | 7 | 3H | 6 | 91.2 | 2.5 | 12 |
| Ex. 5 | DPEA4-HMDI trimer | 39 | 3 | 3H | 2 | 91.5 | 3.1 | 16 |
| Ex. 6 | DPEA6-HMDI trimer | 48 | 2 | 2H | 2 | 92 | 4.2 | 17 |
| Comp. Ex. 1 | PET3-IPDI | 81 | 9 | 2H | 6 | 89.1 | 6.7 | 6 |
| Comp. Ex. 2 | DPHA-IPDI | 107 | 13 | 3H | 9 | 89.9 | 4.4 | 7 |
| Comp. Ex. 3 | HEA-IPDI | 15 | 6 | H | 5 | 90.3 | 10 | 4 |
| Comp. Ex. 4 | HEA-HMDI trimer | 68 | 9 | 2H | 6 | 91.9 | 6.9 | 6 |
| Comp. Ex. 5 | DPHA-HMDI trimer | 142 | 18 | 4H | 10 | 90 | 2.6 | 9 |
| Comp. Ex. 6 | PET3-HMDI trimer | 112 | 14 | 3H | 7 | 90.5 | 3.9 | 8 |

| | | Adhesiveness | | | | Contamination Resistance | | |
|---|---|---|---|---|---|---|---|---|
| | [Steel Wool Resistance] | ABS | PC | PET | acrylic plate | oily ink | hair dye | shoe cream |
| Ex. 1 | A | 100/100 | 100/100 | 30/100 | 100/100 | A | A | A |
| Ex. 2 | A | 100/100 | 100/100 | 50/100 | 100/100 | A | A | A |
| Ex. 3 | B | 100/100 | 100/100 | 80/100 | 100/100 | B | B | A |
| Ex. 4 | A | 100/100 | 100/100 | 20/100 | 100/100 | A | A | A |
| Ex. 5 | A | 100/100 | 100/100 | 40/100 | 100/100 | A | A | A |
| Ex. 6 | B | 100/100 | 100/100 | 70/100 | 100/100 | A | A | A |
| Comp. Ex. 1 | B | 90/100 | 90/100 | 0/100 | 90/100 | B | B | B |
| Comp. Ex. 2 | A | 100/100 | 100/100 | 0/100 | 100/100 | A | A | A |
| Comp. Ex. 3 | C | 80/100 | 90/100 | 0/100 | 90/100 | C | C | C |
| Comp. Ex. 4 | B | 30/100 | 100/100 | 0/100 | 40/100 | B | B | B |
| Comp. Ex. 5 | A | 100/100 | 100/100 | 0/100 | 100/100 | A | A | A |
| Comp. Ex. 6 | B | 50/100 | 100/100 | 0/100 | 50/100 | A | A | A |

From the results shown in Table 1, it was found that the problem of high viscosity that has caused disadvantages in handling and selection of resin composition can be solved by using an alkylene oxide-added (AO-modified) dipentaerythritol (meth)acrylate as the active hydrogen (meth)acrylate for obtaining a urethane acrylate. The photosensitivity tended to increase with the prolongation of the added molar number, but it is in a trade-off relation to the crosslinking density, and the added molar number is therefore preferably 4.

Regarding the foldability, when a polyfunctional (meth) acrylate was used as the reactive component, then the crosslinking density was high and the formed film was rigid, and therefore the film lacked flexibility and was poorly foldable. However, in the urethane acrylate using an AO-modified dipentaerythritol (meth)acrylate as the reactive component, the alkylene oxide chain (AO part) acts as a spacer between the double bonds, and this indicates the possibility that, as the coating layer on a film substrate, the urethane acrylate exhibits high followability without being cracked.

Regarding the curling behavior and the adhesiveness, in Examples using a PET substrate in which adhesiveness is hardly exhibited, both the adhesiveness and the curling behavior were improved with the increase in the added molar number. From this, it is presumed that the curing shrinkage between the double bonds could be suppressed by AO modification, and therefore the adhesiveness reduction and the film deformation owing to the residual inner stress can be suppressed. Regarding the pencil hardness of the cured film, it was found that the pencil hardness lowered with the increase in the added molar number owing to the reduction in the crosslinking density, but it was found that, up to 4 mol, the characteristics of low viscosity could be exhibited without detracting from the hardness. The same may apply to the other evaluation items of scratch resistance, steel wool resistance and contamination resistance.

INDUSTRIAL APPLICABILITY

As described above, the urethane acrylate of the present invention that contains, as the reactive component, an alkylene oxide-modified dipentaerythritol (meth)acrylate which is represented by the above-mentioned general formulae (I)

and (II) and in which the AO-added molar number has been optimized has high photosensitivity and low viscosity excellent in reducibility, and the cured product thereof has high foldability, low curing shrinkage and high hardness. Accordingly, the reactive composition containing, as incorporated therein, a (meth)acrylate of a polyfunctional alcohol such as typically dipentaerythritol, pentaerythritol, ditrimethylolpropane, trimethylolpropane, or the like, or urethaneacrylated with the (meth)acrylate as a reactive component therein can be improved more to have a further lowered viscosity and the physical properties of the cured product of composition can be greatly improved. Consequently, it can be favorably used for resist resin compositions such as dry film resists, color resists, black resists, resists for semiconductors, resin compositions for medical purposes such as dental use, painting/coating resin compositions, printing ink compositions, film coatings, black matrices, photospacers, and the like. In particular, it is expected to exhibit excellent characteristics in use for hard coatings.

The invention claimed is:

1. A urethane acrylate comprising a reaction product of an alkylene oxide-modified dipentaerythritol (meth)acrylate having a structure represented by the following general formulae (I) and (II), and a polyisocyanate:

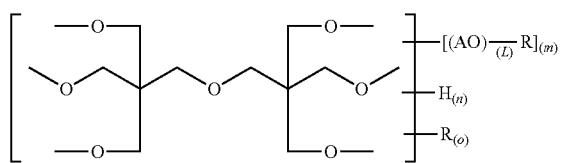

(I)

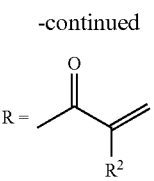

(II)

wherein in the general formula (I), R represents a substituent represented by the general formula (II), AO indicates one or two or more selected from alkylene oxide units represented by $-CH_2CH_2O-$, $-CH_2CH(CH_3)O-$, $-CH_2CH_2CH_2CH_2O-$ or $-CH_2CH(C_2H_5)O-$, a mean value of L indicating a mean degree of polymerization of added alkylene oxides is more than 0 and 1 or less, a mean value of m is more than 0 and 5 or less, a mean value of n is 1 or more and less than 6, a mean value of o is 0 or more and 5 or less, and a total of m, n and o is 6; and wherein in the general formula (II), $R^2$ represents a hydrogen atom or a methyl group.

2. A reactive composition comprising the urethane acrylate described in claim 1.

3. A urethane acrylate according to claim 1 having a mean added molar number of ethylene oxide of 2 to 4.

4. A reactive composition comprising the urethane acrylate described in claim 3.

* * * * *